(12) United States Patent
Barcelo et al.

(10) Patent No.: US 9,739,717 B2
(45) Date of Patent: Aug. 22, 2017

(54) FORMING 3-D NANO-PARTICLE ASSEMBLIES

(71) Applicant: Hewlett-Packard Development Company, L.P., Houston, TX (US)

(72) Inventors: Steven J. Barcelo, Palo Alto, CA (US); Zhiyong Li, Foster City, CA (US); Ansoon Kim, Mountain View, CA (US); Zhang-Lin Zhou, San Diego, CA (US); Gary Gibson, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 15/289,050

(22) Filed: Oct. 7, 2016

(65) Prior Publication Data
US 2017/0023483 A1  Jan. 26, 2017

Related U.S. Application Data

(62) Division of application No. 13/754,404, filed on Jan. 30, 2013, now Pat. No. 9,476,833.

(51) Int. Cl.
*G01N 21/65* (2006.01)
*B82Y 40/00* (2011.01)

(52) U.S. Cl.
CPC ............ *G01N 21/658* (2013.01); *B82Y 40/00* (2013.01); *Y10S 977/882* (2013.01)

(58) Field of Classification Search
CPC .... G01N 21/658; B82Y 40/00; Y10S 977/882
See application file for complete search history.

(56) References Cited

U.S. PATENT DOCUMENTS

| | | | |
|---|---|---|---|
| 7,727,776 B2 | 6/2010 | Zhou et al. | |
| 7,776,425 B2 | 8/2010 | Kalkan et al. | |
| 8,767,202 B2 | 7/2014 | Schmidt et al. | |
| 2011/0165077 A1 | 7/2011 | Qian et al. | |
| 2012/0050732 A1 | 3/2012 | Lu et al. | |
| 2012/0208315 A1 | 8/2012 | Sargent et al. | |

OTHER PUBLICATIONS

Hudson, Stephen D. "Synthesis, characterization, and application of Ag nanostructures." PhD diss., Clemson University, Dec. 4, 2009.

*Primary Examiner* — Sam P Siefke
(74) *Attorney, Agent, or Firm* — Mannava & Kang, P.C.

(57) ABSTRACT

According to an example, methods for forming three-dimensional (3-D) nano-particle assemblies include depositing SES elements onto respective tips of nano-fingers, in which the nano-fingers are arranged in sufficiently close proximities to each other to enable the tips of groups of adjacent ones of the nano-fingers to come into sufficiently close proximities to each other to enable the SES elements on the tips to be bonded together when the nano-fingers are partially collapsed. The methods also include causing the nano-fingers to partially collapse toward adjacent ones of the nano-fingers to cause a plurality of SES elements on respective groups of the nano-fingers to be in relatively close proximities to each other and form respective clusters of SES elements, introducing additional particles that are to attach onto the clusters of SES elements, and causing the clusters of SES elements to detach from the nano-fingers.

20 Claims, 10 Drawing Sheets

FORMING 3-D NANO-PARTICLE ASSEMBLIES

CROSS-REFERENCE TO RELATED PATENT APPLICATIONS

The present application is a divisional application claiming priority under 35 USC section 120 from co-pending U.S. patent application Ser. No. 13/754,404 filed on Jan. 30, 2013 by Barcelo, et al. and entitled FORMING 3-D NANO-PARTICLE ASSEMBLIES, the full disclosure of which is hereby incorporated by reference.

BACKGROUND

In surface-enhanced spectroscopy (SES), such as surface-enhanced Raman spectroscopy (SERS), vibrationally or electronically excitable levels of an analyte are probed. The energy of a photon can shift by an amount equal to that of the vibrational level excited by the photon (Raman scattering). A Raman spectrum, which consists of a wavelength distribution of bands corresponding to molecular vibrations specific to the analyte being probed, may be detected to identify the analyte. In SERS, the analyte molecules are in close proximity, for instance, less than tens of nanometers, to metal nano-particles that may be or may not be coated with a dielectric, such as silicon dioxide, silicon nitride, and a polymer, that, once excited by light, set up plasmon modes, which create near fields around the metal nano-particles. These fields can couple to analyte molecules in the near field regions. As a result, concentration of the incident light occurs at close vicinity to the nano-particles, enhancing the emission of scattered signals from the analyte molecules.

BRIEF DESCRIPTION OF THE DRAWINGS

Features of the present disclosure are illustrated by way of example and not limited in the following figure(s), in which like numerals indicate like elements, in which.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are methods for forming three-dimensional (3-D) nano-particle assemblies and 3-D nano-particle assemblies that may be formed through implementation of the methods. As described in greater detail herein below, the methods may include the use of a plurality of nano-fingers onto which a plurality of surface-enhanced spectroscopy (SES) elements may be deposited. Through partial collapsing of the nano-fingers onto other ones of the nano-fingers, for instance, in a controlled manner, the SES elements positioned on various groups of the nano-fingers may be brought into sufficiently close proximities to enable those SES elements to be bonded together in a designed geometry. In one regard, the use of the nano-fingers in bonding respective groups of SES elements together generally enables the groups of SES elements to be arranged in relatively tighter packed configurations than may be possible with conventional methods of SES element bonding.

Following bonding of the respective groups of SES elements to each other to form respective clusters, additional particles that are to attach onto the clusters may be introduced. The additional particles may be attached to the clusters to form the 3-D nano-particle assemblies disclosed herein. Additionally, a reporter molecule may be trapped between the SES elements as they are formed into the clusters. In some examples, the reporter molecule may be a binding molecule that is to bond the SES elements in the clusters.

According to an example, protective coatings may be provided on surfaces of the 3-D nano-particle assemblies disclosed herein. In addition, the protective coatings may be functionalized to preferentially bond to specific regions, e.g., target tissues/cells in a human body. Thus, for instance, the 3-D nano-particle assemblies disclosed herein may be employed to map locations of the specific regions.

Generally speaking, conventional Raman based tagging structures are typically composed of a Raman reporter molecule trapped in the "hot spot" of plasmonic nano-particle assemblies that typically have two-dimensional dimer or trimer structures. A similar configuration may be used for fluorescence reporter molecules. When the hot spot is excited by laser light of the appropriate wavelength, the reporter molecule may emit a signature radiation pattern that is enhanced due to its location in the hot spot. These hot spots typically have a strong polarization dependence, particularly in the dimer structures most commonly used. However, the excitation light source is typically randomly polarized, and conventional tagging structures are also randomly oriented. As such, because of the strong polarization dependence, the use of conventional tagging structures often results in weak signals and low contrast.

The 3-D nano-particle assemblies disclosed herein may be substantially less dependent upon the polarization of the excitation light and the orientations of the 3-D nano-particle assemblies as compared with conventional tagging structures. In addition, or alternatively, the 3-D nano-particle assemblies disclosed herein may be fabricated to have predetermined polarization attributes that, for instance, may substantially be aligned with the excitation light. In any regard, therefore, the 3-D nano-particle assemblies disclosed herein may be able to achieve relatively stronger enhancement and thus better imaging as compared with conventional tagging structures. In addition, through implementation of the forming methods disclosed herein, the 3-D nano-particle assemblies disclosed herein may be formed to have substantially uniform configurations with respect to each other. The substantial uniformity of the 3-D nano-particle assemblies may also result in more consistent enhancement and thus more consistent detection as compared with 3-D particle assemblies having random configurations. In another regard, therefore, the methods disclosed herein may be implemented to engineer 3-D particle assemblies having specific geometries that significantly enhance signal emissions from, for instance, the reporter molecules contained in the 3-D particle assemblies.

Figures 1A, 1B:
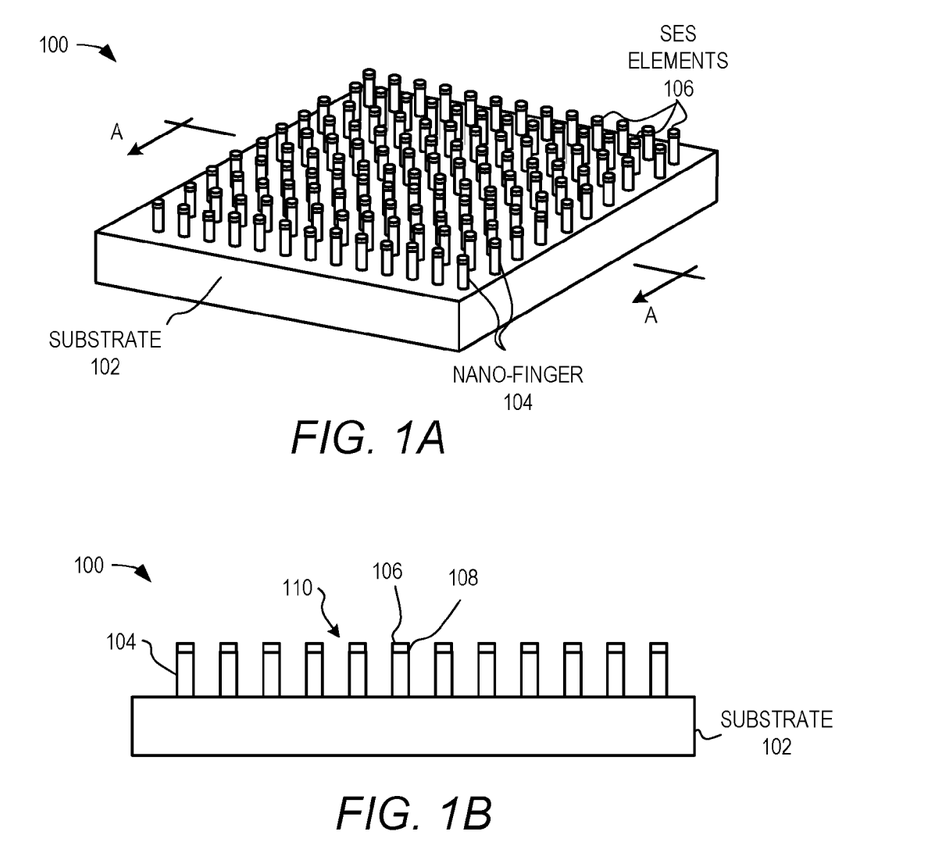
FIG. 1A shows an isometric view of an apparatus for forming three-dimensional (3-D) nano-particle assemblies, according to an example of the present disclosure.
FIGS. 1B and 1C, respectively show cross-sectional views along a line A-A of the apparatus shown in FIG. 1A, prior to and following partial collapse of the nano-fingers contained in the apparatus, according to examples of the present disclosure.
Figure 1C:
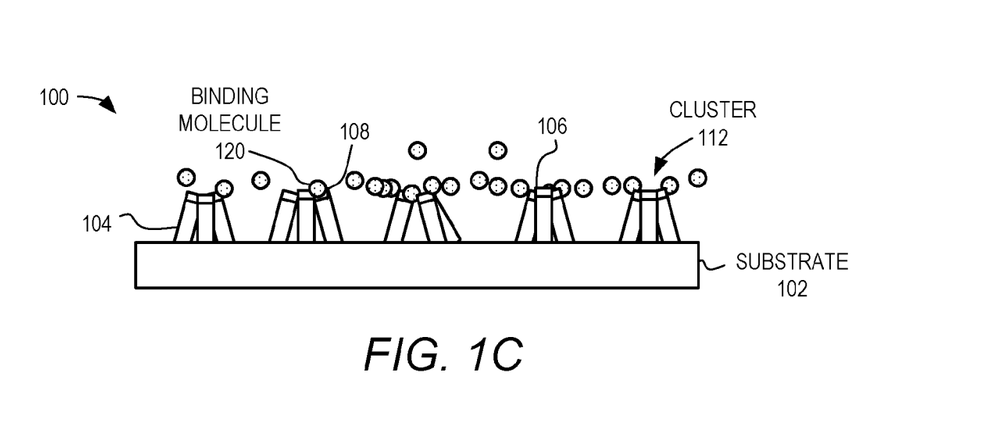

With reference first to FIGS. 1A-1C, there are respectively shown an isometric view and cross-sectional views taken along lines A-A of FIG. 1A of an apparatus 100 for forming three-dimensional (3-D) nano-particle assemblies, according to an example. It should be understood that the apparatus 100 depicted in FIGS. 1A-1C may include additional components and that some of the components described herein may be removed and/or modified without departing from a scope of the apparatus 100 disclosed herein. It should also be understood that the components depicted in FIGS. 1A-1C are not drawn to scale and thus, the components may have different relative sizes with respect to each than as shown therein.

An example of a 3-D nano-particle assembly that may be formed through implementation of the apparatus 100 may include a base cluster of surface-enhanced spectroscopy (SES) elements 106 on which an additional particle, such as a functional molecule or another base cluster of SES elements 106, may be attached. The base cluster of SES elements 106 may be attached to each other substantially along the first plane and the additional particle may be attached to the base cluster of SES elements 106 on a second plane that is different from the first plane, thereby forming the 3-D nano-particle assembly.

As shown in FIG. 1A, the apparatus 100 includes a substrate 102, which may be formed of a material, such as, silicon, silicon nitride, glass, plastic, polymer, $SiO_2$, $Al_2O_3$, aluminum, etc., or a combination of these materials, etc. In addition, a plurality of nano-fingers 104 are depicted as extending above a surface of the substrate 102 and a plurality of SES elements 106 are depicted as being positioned on the tips of respective nano-fingers 104.

According to an example, the nano-fingers 104 may have dimensions that are in the nanometer range, for instance, dimensions that may be less than about 500 nm, and may be formed of a relatively flexible material to enable the nano-fingers 104 to be laterally bendable or collapsible, for instance, to enable tips of the nano-fingers 104 to move toward each other, as discussed in greater detail herein below. Examples of suitable materials for the nano-fingers 104 may include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 104 may be attached to the surface of the substrate 102 through any suitable attachment mechanism. For instance, the nano-fingers 104 may be grown directly on the substrate 102 surface through implementation of any of a variety of suitable nano-structure growing techniques. As another example, the nano-fingers 104 may be integrally formed with the substrate 102. In this example, for instance, a portion of the material from which the substrate 102 is fabricated may be etched or otherwise processed to form the nano-fingers 104. In a further example, a separate layer of material may be adhered to the substrate 102 surface and the separate layer of material may be etched or otherwise processed to form the nano-fingers 104. In various examples, the nano-fingers 104 may be fabricated through a nanoimprinting or an embossing process in which a template of relatively rigid pillars may be employed in a multi-step imprinting process on a polymer matrix to form the nano-fingers 104. In these examples, a template may be formed through photolithography or other advanced lithography with the desired patterning to arrange the nano-fingers 104 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (polydimethylsiloxane (PDMS), polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 104.

The nano-fingers 104 have been depicted as having substantially cylindrical cross-sections. It should, however, be understood that the nano-fingers 104 may have other shaped cross-sections, such as, for instance, rectangular, square, triangular, etc. In addition, or alternatively, the nano-fingers 104 may be formed with a feature, such as, notches, bulges, etc., to substantially cause the nano-fingers 104 to be inclined to collapse in particular directions. Thus, for instance, two or more adjacent nano-fingers 104 may include features to increase the likelihood that the nano-fingers 104 collapse toward each other. According to a particular example, groups of three or more adjacent nano-fingers 104 include features or may otherwise be fabricated to collapse toward each other, such that the tips on the three or more adjacent nano-fingers 104 may come into close contact with each other when the nano-fingers 104 are partially collapsed. Various manners in which the nano-fingers 104 may be partially collapsed are described in greater detail herein below.

The apparatus 100 includes a substantially random distribution of nano-fingers 104 or a predetermined configuration of nano-fingers 104. In any regard, according to an example, the nano-fingers 104 may be arranged with respect to each other such that the tips of at least two neighboring nano-fingers 104 are able to be brought into close proximity with each other when the nano-fingers 104 are in a partially collapsed state. By way of particular example, the neighboring nano-fingers 104 may be positioned less than about 100 nanometers apart from each other. According to a particular example, the nano-fingers 104 may be patterned on the substrate 102 such that neighboring ones of the nano-fingers 104 preferentially partially collapse into predefined geometries, for instance, triangles, squares, pentagons, etc. In this regard, the number of SES elements 106 being formed into respective clusters 112 may substantially be controlled through control of the patterning of the nano-fingers 104.

Turning now to FIG. 1B, there is shown a cross-sectional view along a line A-A in FIG. 1A of the apparatus 100, in accordance with an example. As shown therein, each of the tips 108 of the nano-fingers 104 includes a respective SES element 106 disposed thereon. The SES elements 106, which may include metallic nanoparticles as discussed below, may be deposited onto the tips 108 of the nano-fingers 104 through one of, for instance, physical vapor deposition (PVD), chemical vapor deposition (CVD), sputtering, etc., of metallic material, or self-assembly of pre-synthesized nano-particles.

Generally speaking, the SES elements 106 may be elements that enhance the emission of any of light, fluorescence, luminescence, etc., by particles in relatively close proximities to the SES elements 106 and therefore enhance sensing operations, such as surface enhanced Raman spectroscopy (SERS), enhanced photoluminescence, enhanced fluorescence, etc., on the particles. The SES elements 106 may include plasmonic nanoparticles or nanostructures, which may be plasmon-supporting materials such as but not limited to, gold (Au), silver (Ag), and copper (Cu).

The SES elements 106 may have nanoscale surface roughness, which may generally be characterized by nanoscale surface features on the surface of the layer(s) and may be produced spontaneously during deposition of the plasmon-supporting material layer(s). By definition herein, a plasmon-supporting material may be a material that facilitates scattering of signals and the production or emission of a signal from an analyte on or near the material during spectroscopy.

In some examples, the SES elements 106 may be functionalized to facilitate adsorption of target molecules. For example, surfaces of the SES elements 106 may be functionalized such that a particular class of analytes may be attracted to and may bond or be preferentially adsorbed onto the SES elements 106. By way of particular example, the SES elements 106 may be functionalized to attach to target molecules that may be contained in, for instance, particular types of cells, tissues, etc.

Although the nano-fingers 104 have been depicted in FIGS. 1A-1B as each extending vertically and at the same heights with respect to each other, it should be understood that some of the nano-fingers 104 may extend at various angles and heights with respect to each other. The differences in angles and/or heights between the nano-fingers 104 may occur, for instance, due to differences arising from manufacturing or growth variances existent in the fabrication of the nano-fingers 104 and the deposition of the SES elements 106 on the nano-fingers 104, etc.

As shown in FIG. 1B, the nano-fingers 104 are in a first position, in which the tips 108 are in a substantially spaced arrangement with respect to each other. The gaps 110 between the tips 108 may be of sufficiently large size to enable a liquid to be positioned in the gaps 110. In addition, the gaps 110 may be of sufficiently small size to enable the tips 108 of at least some of the nano-fingers 104 to be drawn toward each other as the liquid provided in the gaps 110 evaporates, through, for instance, capillary forces applied on the tips 108 as the liquid evaporates.

Turning now to FIG. 1C, there is shown a cross-sectional view along a line A-A, shown in FIG. 1A, of the apparatus 100, following evaporation of the liquid, according to an example. The view depicted in FIG. 1C is identical to the view depicted in FIG. 1B, except that the nano-fingers 104 are depicted in a second position, in which the tips 108 of some of the nano-fingers 104 have been drawn toward with each other. According to an example, the tips 108 of some of the nano-fingers 104 may be in and may remain in relatively close proximity to each other for a period of time due to the capillary forces applied on adjacent ones of the nano-fingers 104 during and following evaporation of the liquid (not shown) in the gaps 110 between the tips 108.

In one regard, the partial collapse of the nano-fingers 104 may cause the SES elements 106 positioned on the adjacent tips 108 of the nano-fingers 104 that have partially collapsed toward each other to come into relatively close proximities with respect to each other and in some instances, to contact each other. According to an example, the SES elements 106 may include gold and the contacting SES elements 106 may bond to each other through gold-gold bonding. According to another example, the SES elements 106 may include any of gold, silver, platinum, etc., and the SES elements 106 that are on adjacent tips 108 of the nano-fingers 104 may bond to each other through binding molecules 120, such as dithiol, diamine, etc. In this example, the fluid that may be used to partially collapse the nano-fingers 104 may include a solution containing the binding molecules 120, such that the binding molecules 120 may bind the SES elements 106 that are in relatively close proximities to each other, i.e., SES elements 106 on adjacent tips 108 of a group of partially collapsed nano-fingers 104.

As also shown in FIG. 1C, the SES elements 106 may be formed into clusters 112 of SES elements 106. In some examples, the SES elements 106 and the binding molecules 120 may collectively be formed into the clusters 112. According to an example, the binding molecules 120 may be reporter molecules, such as Raman tags, fluorescence tags, etc. By way of particular example, the binding molecules 120 may be 4,4'-thiobisbenzenethiol (TBBT) tags. In other examples, the reporter molecules may be separate molecules that may be trapped between the SES elements 106 in the clusters 112.

Figure 1D:
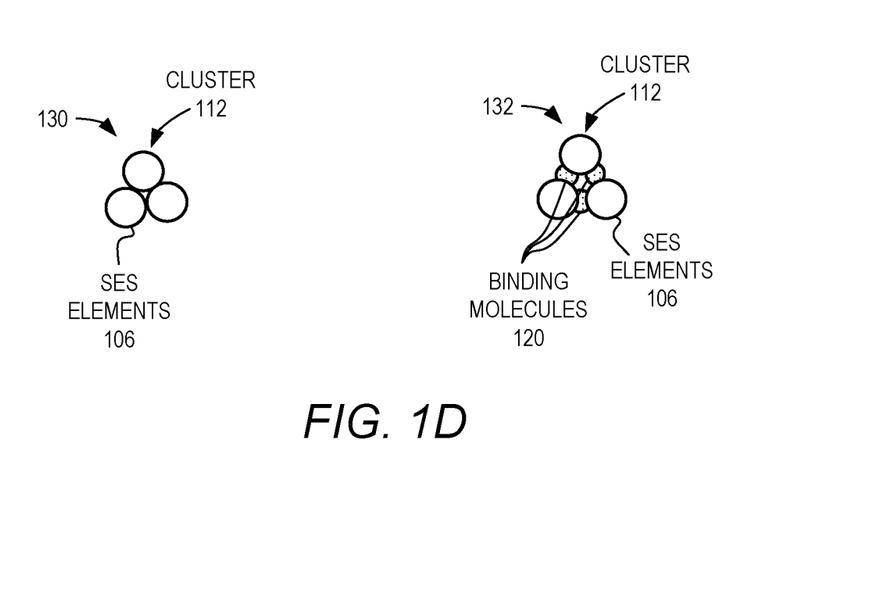
FIGS. 1D and 1E, respectively show diagrams of various example configurations of SES elements, and in some instances, binding molecules, according to various examples of the present disclosure.
Figure 1E:
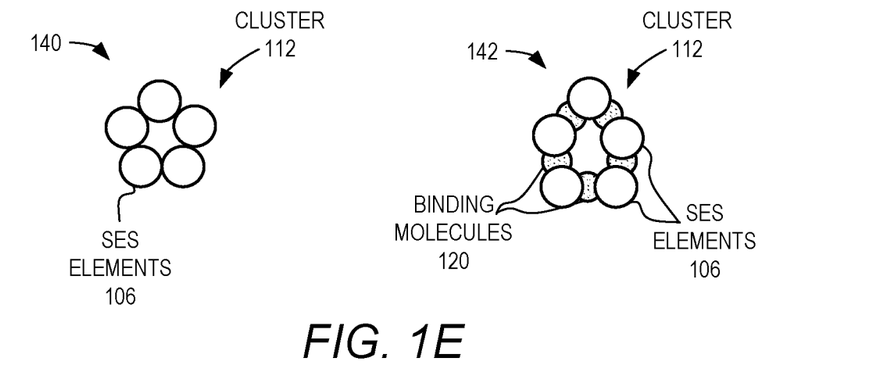

Turning now to FIGS. 1D and 1E, there are shown diagrams of various example configurations of the SES elements 106, and in some instances, the binding molecules 120, according to various examples. Generally speaking, the diagrams depicted in FIGS. 1D and 1E illustrate examples of possible arrangements of the SES elements 106 (and the binding molecule 120) that may result when the nano-fingers 104 are partially collapsed as shown in FIG. 1C. It should thus be understood that the diagrams depicted in FIGS. 1D and 1E are provided merely for purposes of illustration and that therefore any number of alternate configurations, which may include other numbers of SES elements 106 and/or binding molecules 120, may be formed without departing from scopes of examples of the present disclosure.

With reference first to FIG. 1D, the first diagram 130 illustrates an example in which three SES elements 106 may be bonded together, for instance, through gold-gold bonding, to form the cluster 112. The second diagram 132 illustrates an example in which three SES elements 106 may be bonded together through binding molecules 120 to form the cluster 112, and in which the SES elements 106 do not contact each other.

With reference now to FIG. 1E, the first diagram 140 illustrates an example in which five SES elements 106 may be bonded together, for instance, through gold-gold bonding, to form the cluster 112. The second diagram 142 illustrates an example in which five SES elements 106 may be bonded together through binding molecules 120 to form the cluster 112. Additionally, in a cluster 112, some of the SES elements 106 may be bonded to each other through gold-gold bonding while others of the SES elements 106 may be bonded to each other through binding molecules 120.

Figure 2:
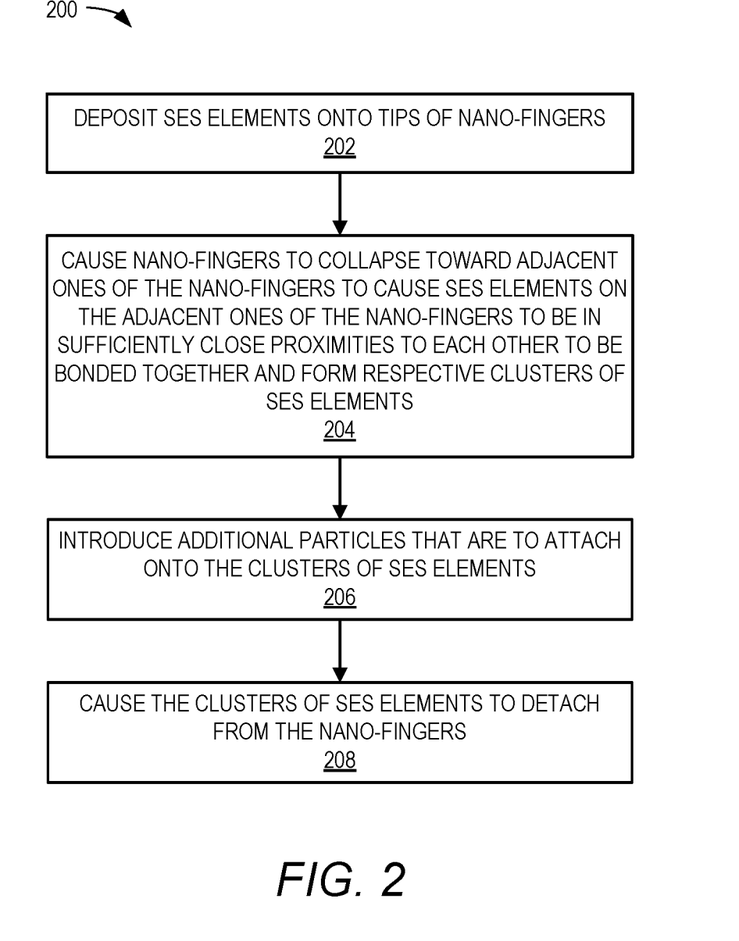
FIG. 2 shows a flow diagram of a method for forming 3-D nano-particle assemblies, according to an example of the present disclosure.

Turning now to FIG. 2, there is shown a flow diagram of a method 200 for forming three-dimensional (3-D) nano-particle assemblies, according to an example. It should be understood that the method 200 depicted in FIG. 2 may include additional processes and that some of the processes described herein may be removed and/or modified without departing from a scope of the method 200.

At block 202, a plurality of SES elements 106 may be deposited onto the tips 108 of a plurality of nano-fingers 104, in which the plurality of nano-fingers 104 extend from a substrate 102 and may be arranged in sufficiently close proximities to each other to enable the tips 108 of groups of adjacent ones of the plurality of nano-fingers 104 to come into sufficiently close proximities to each other to enable the SES elements 106 on the tips 104 to be bonded together when the nano-fingers 104 are partially collapsed. That is, the plurality of nano-fingers 104 may be in sufficiently close proximities to each other to enable the SES elements 106 on the tips 104 of respective groups of nano-fingers 104, for instance, three or more, to be bonded to each other through either or both of gold-gold bonding and binding molecules 120.

At block 204, the nano-fingers 104 may be caused to partially collapse toward adjacent ones of the nano-fingers to cause the SES elements 106 on respective groups of the nano-fingers 104 to be in relatively close proximities to each other and form respective clusters 112 of SES elements 106. As discussed above, the nano-fingers 104 may be fabricated on the substrate 102 such that the nano-fingers 104 in respective groups partially collapse toward each other (and thus not toward nano-fingers 104 in other groups). As also discussed above, the nano-fingers 104 may be caused to partially collapse toward each other through introduction and removal of a fluid between the nano-fingers 104.

At block 206, additional particles that are to attach onto the clusters of SES elements may be introduced onto the clusters 112 of SES elements 106. As described in greater detail below, the additional particles may be introduced onto the clusters 112 of SES elements 106 while the clusters 112 of SES elements 106 may be on the tips 108 of the nano-fingers 104. In other examples, the additional particles may be introduced onto the clusters 112 following detachment of the clusters 112 from the tips 108 of the nano-fingers 104. The additional particles may bond with the clusters 112 to form the 3-D nano-particle assemblies as discussed in greater detail below.

At block 208, the clusters 112 of SES elements 106 may be caused to detach from the tips 108 of the nano-fingers 104. The clusters 112 of SES elements 106 may be caused to detach from the tips 108 of the nano-fingers 104 in a variety of manners, various examples of which are described below. In addition, the 3-D nano-particle assemblies may be formed before, during, and/or after detachment of the clusters 112 as discussed with respect to the following examples.

Figure 3A:
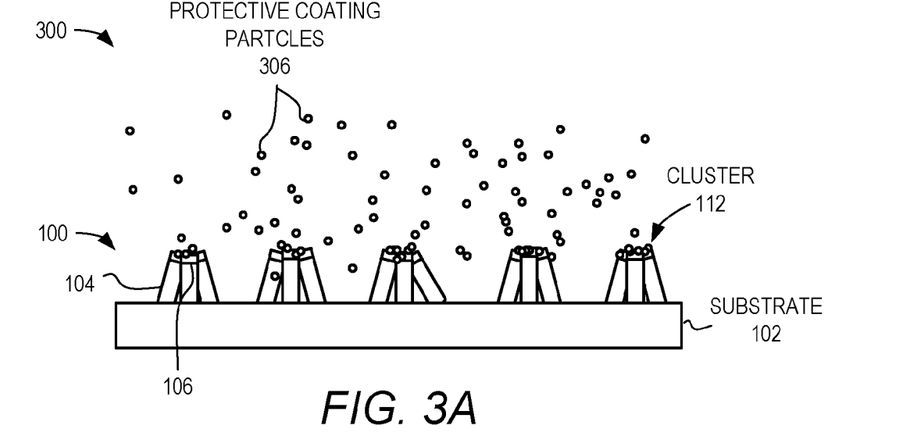
FIGS. 3A-3C, 4A-4C, 5A-5C, 6A-6B, 7A-7B, 8A-8C, and 9A-9C, respectively show diagrams of various stages of methods for forming 3-D nano-particle assemblies, according to examples of the present disclosure.
Figure 3B:
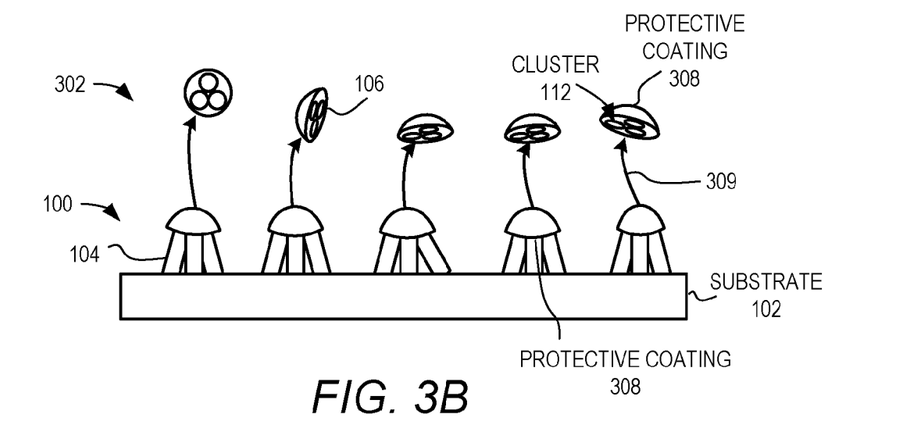
Figure 3C:
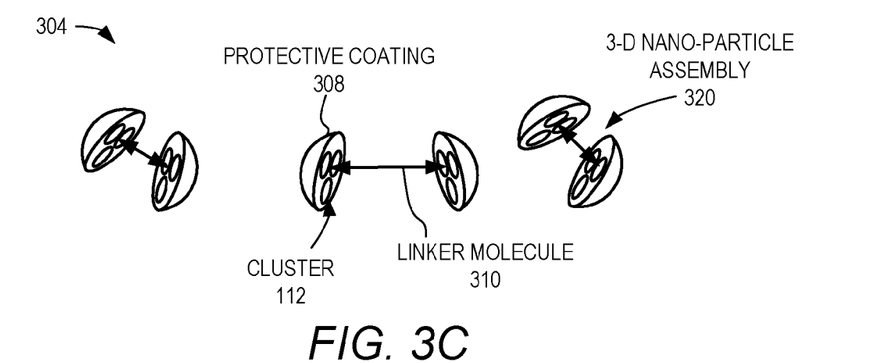

Turning now to FIGS. 3A-3C, there are respectively shown diagrams 300, 302, 304 of various stages of a method for forming 3-D nano-particle assemblies 320, according to an example. As shown in the diagram 300, additional particles, in this example, a plurality of protective coating particles 306, may be introduced onto the clusters 112 of SES elements 106. The protective coating particles 306 may be introduced onto the clusters 112 through any suitable deposition technique, such as through spraying of the protective coating particles 306, through implementation of an inkjet-like apparatus, etc.

According to an example, the protective coating particles 306 may include silicon oxide or other type of oxide. In addition, the protective coating particles 306 may combine to form a protective coating 308 on the exposed sides of the clusters 112 as half-shells of protective coatings 308 on the clusters 112 as shown in the diagram 302 in FIG. 3B. The diagram 302 also shows that the clusters 112, along with the protective coatings 308, may be detached from the nano-fingers 104, as denoted by the arrows 309. The diagram 302 further shows that the bottoms of SES elements 106 that were in contact with the tips 108 of the nano-fingers 104 may be exposed in the detached clusters 112. Although not shown in FIG. 3B, the clusters 112 may be released into a solution.

As shown in the diagram 304, linker molecules 310 may be introduced onto the clusters 112. The linker molecules 310 may include any suitable type of molecule that is to link SES elements 106 together. By way of example, the linker molecules 310 may be dithiol, diamine, etc. As shown in the diagram 304 (FIG. 3C), the linker molecules 304 may link the exposed portions of multiple clusters 112 to form 3-D nano-particle assemblies 320. According to an example, the 3-D nano-particle assemblies 320 may be implemented in biological imaging application, in which the protective coating 308 may protect the clusters 112 of SES elements 106 during and after insertion of the 3-D nano-particle assemblies 320 in a sample, such as a human body. In addition, an additional material (not shown) may be applied onto the protective coating 308 and/or the protective coating 308 may otherwise be functionalized to attach to target molecules inside of the sample. According to an example, the protective coating 308 may protect the SES elements 106 from various materials contained in the sample, such as, certain proteins, cells, etc. In this regard, although the 3-D nano-particle assemblies 320 have been depicted as having gaps between the clusters 112, the linker molecules 310 may bond the clusters 112 with a relatively small gap therebetween to substantially prevent the materials in the sample from contacting the SES elements 106.

Figure 4A:
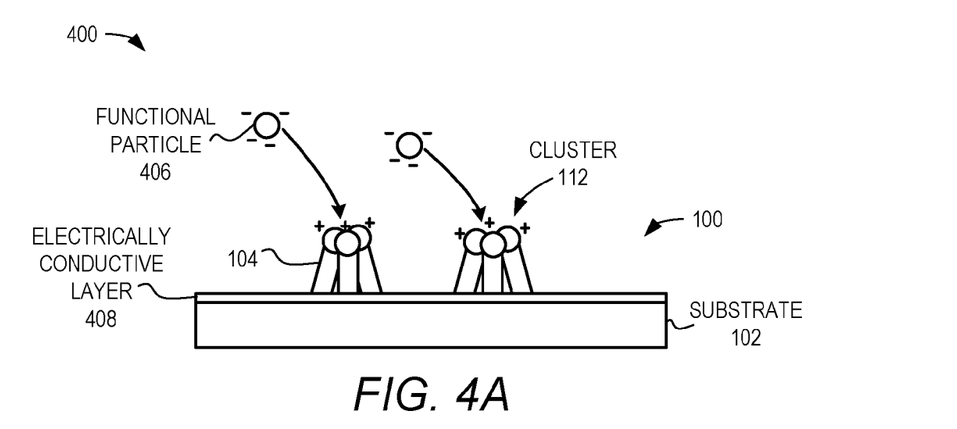
Figure 4B:
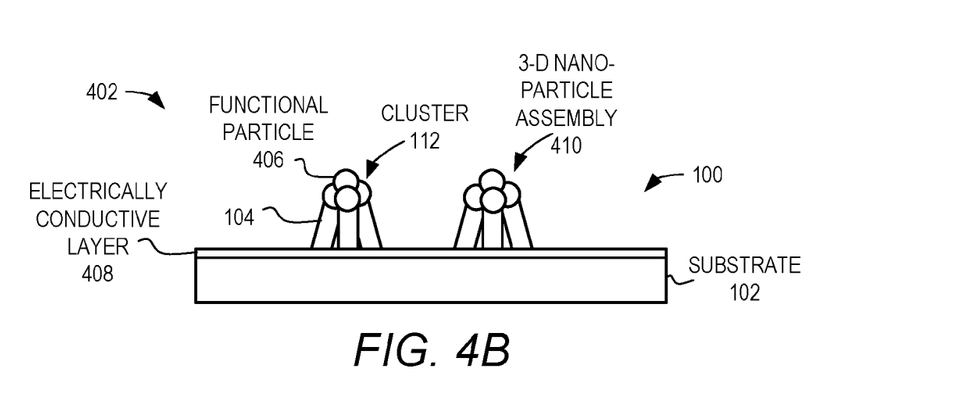
Figure 4C:
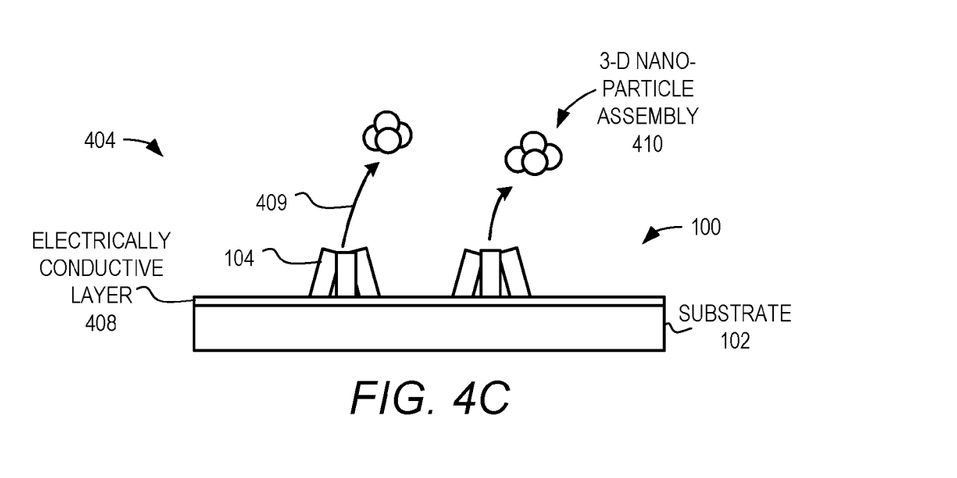

Turning now to FIGS. 4A-4C, there are respectively shown diagrams 400, 402, 404 of various stages of a method for forming 3-D nano-particle assemblies 410, according to an example. As shown in the diagram 400 (FIG. 4A), additional particles, in this example, functional particles 406, may be introduced onto the clusters 112 of SES elements 106. According to an example, the functional particles 406 may be particles that are similar to the SES elements 106. In another example, the functional particles 406 may be particles that are to afford other functions to the 3-D nano-particle assemblies 410. By way of example, the functional particles 406 may be functionalized to attach to target molecules that may be contained in, for instance, particular types of cells, tissues, etc.

In any regard, the functional particles 406 are depicted in the diagram 400 as including a particular electrical charge, in this case a negative electrical charge. In addition, the apparatus 100 is depicted as including an electrically conductive layer 408 provided on the substrate 102. Moreover, an oppositely biased electrical charge, in this case a positive electrical charge, may be applied on the clusters 112 of SES elements 106 when a voltage is applied through the electrically conductive layer 408. The opposite biases of the functional particles 406 and the clusters 112 of SES elements 106 may generally cause the functional particles 406 to be attracted to and contact the clusters 112 of SES elements 106. The functional particles 406 may also bond with the SES elements 106 through gold-gold bonding, a binding molecule, and/or through an electrostatic force that may remain between the functional particles 406 and the SES elements 106 following cessation of the applied voltage on the electrically conductive layer 408.

As shown in the diagram 402 (FIG. 4B), the combinations of the functional particles 406 and the respective clusters 112 may form the 3-D nano-particle assemblies 410. In addition, as shown in the diagram 404 (FIG. 4C), the 3-D nano-particle assemblies 410 may be caused to be detached from the nano-fingers 104, as denoted by the arrows 409. The 3-D nano-particle assemblies 410 may be caused to be detached from the nano-fingers 104 through any suitable detachment techniques, some of which are described below.

Figure 5A:
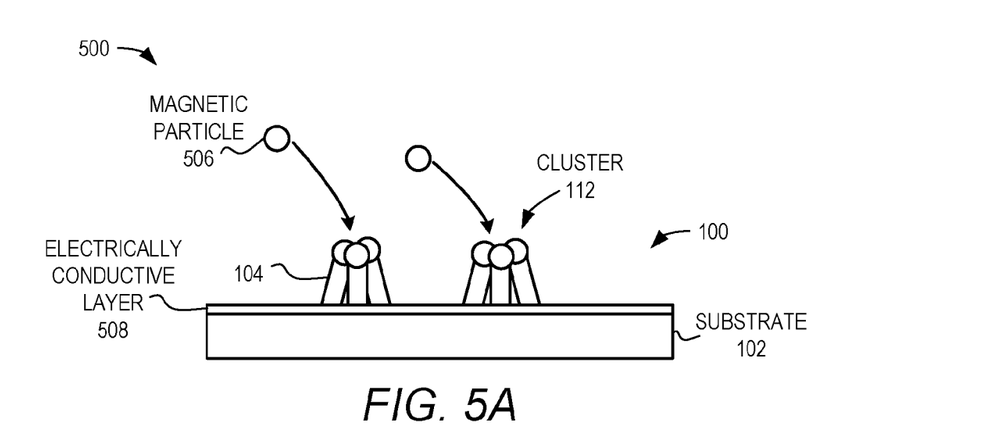
Figure 5B:
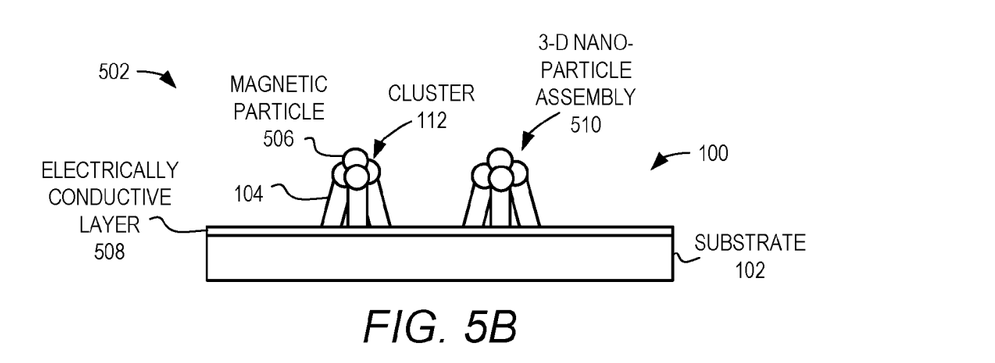
Figure 5C:
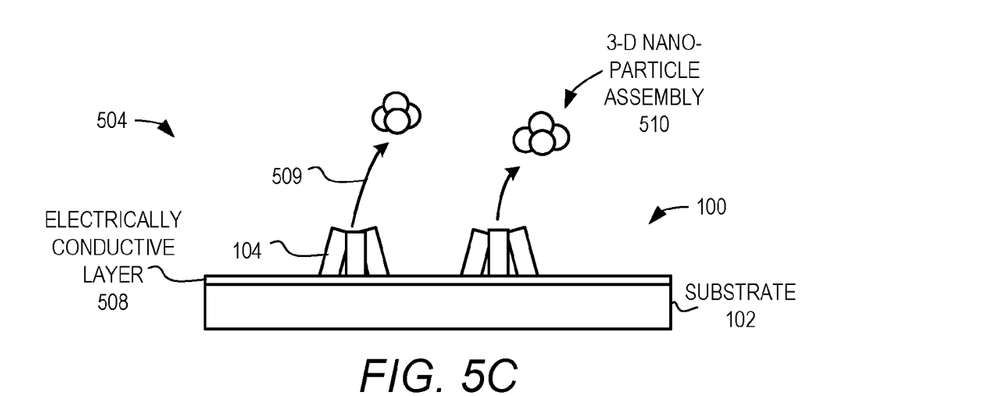

Turning now to FIGS. 5A-5C, there are respectively shown diagrams 500, 502, 504 of various stages of a method for forming 3-D nano-particle assemblies 510, according to an example. As shown in the diagram 500 (FIG. 5A), additional particles, in this example, magnetic particles 506, may be introduced onto the clusters 112 of SES elements 106. According to an example, the magnetic particles 506 may be particles that are similar to the SES elements 106. In another example, the magnetic particles 506 may be particles that are to afford other functions to the 3-D nano-particle assemblies 510. By way of example, the magnetic particles 506 may be functionalized to attach to target molecules that may be contained in, for instance, particular types of cells, tissues, etc.

The magnetic particles 506 may be particles that are entirely magnetic or particles having magnetic cores and shells that may be non-magnetic. For instance, the magnetic particles 506, or the cores thereof, may include magnetic materials, such as, nickel, iron, cobalt, gadolinium, etc. In instances where the magnetic particles 506 include magnetic cores, the shells thereof may include a material and may be functionalized in manners similar to the SES elements 106 and may thus include, for instance, gold, silver, copper, etc. In addition, the SES elements 106 may have similar configurations, e.g., magnetic cores surrounded by functionalized shells.

In any regard, the magnetic particles 506 may be attracted to the SES elements 106 and may contact the SES elements 106 due the magnetic forces of both the SES elements 106 and the magnetic particles 506. The magnetic forces may substantially be enhanced through application of a voltage through the electrically conductive layer 508, which may cause an electromagnetic force to be generated around the SES elements 106. The magnetic particles 506 may also bond with the SES elements 106 through gold-gold bonding or a binding molecule 120.

As shown in the diagram 502 (FIG. 5B), the combinations of the magnetic particles 506 and the respective clusters 112 may form the 3-D nano-particle assemblies 510. In addition, as shown in the diagram 504 (FIG. 5C), the 3-D nano-particle assemblies 510 may be caused to be detached from the nano-fingers 104, as denoted by the arrows 509. The 3-D nano-particle assemblies 510 may be caused to be detached from the nano-fingers 104 through any suitable detachment techniques, some of which are described below.

Figure 6A:
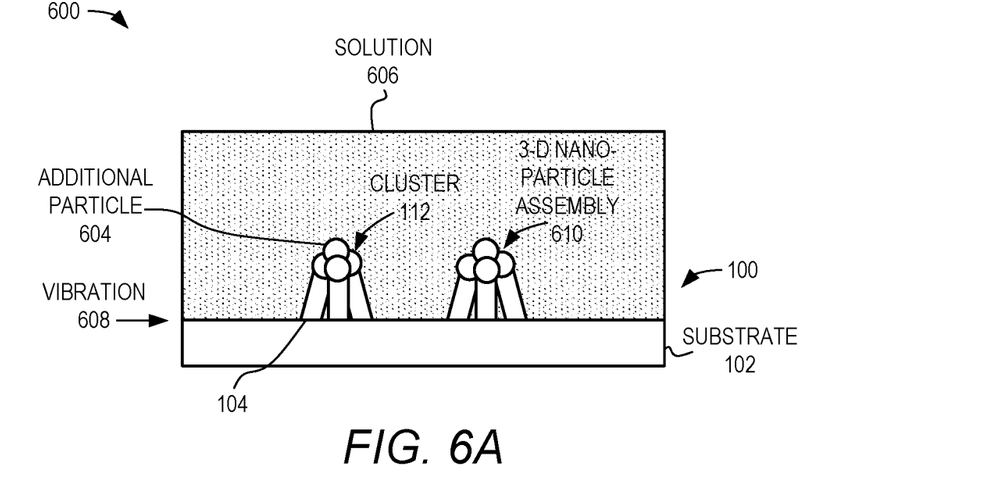
Figure 6B:
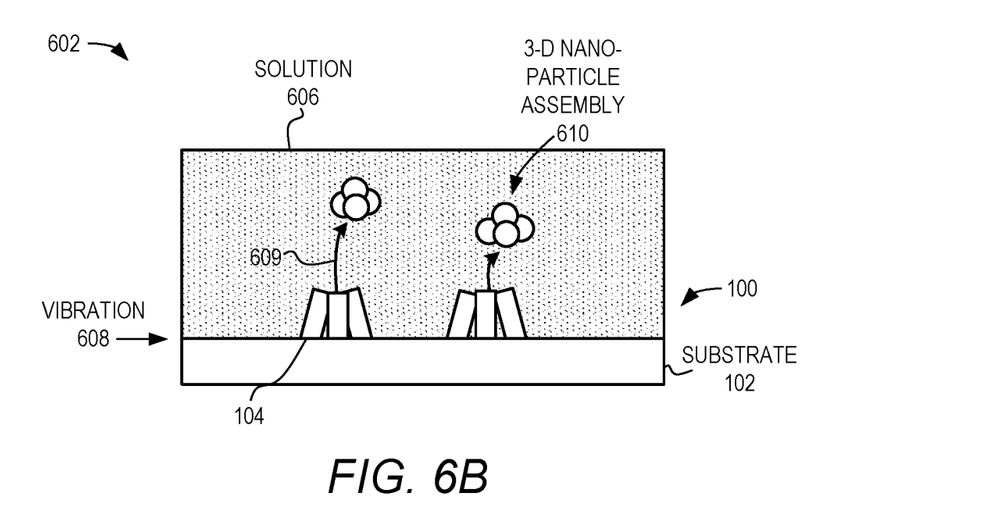

Turning now to FIGS. 6A and 6B, there are respectively shown diagrams 600 and 602 of various stages of a method for forming 3-D nano-particle assemblies 610, according to an example. As shown in the diagram 600 (FIG. 6A), additional particles 604 are depicted as having bonded with the clusters 112 to form 3-D nano-particle assemblies 610. The additional particles 604 may be bonded to the clusters 112 in any of the manners discussed above. In this regard the 3-D nano-particle assemblies 610 may include any of the 3-D nano-particle assemblies 410 and 510 discussed above with respect to FIGS. 4A-5C.

In addition, the apparatus 100, along with the 3-D nano-particle assemblies 610, are depicted as being positioned in a solution 606. The solution 606 may include any suitable type of material into which the 3-D nano-particle assemblies 610 may be released. Thus, for instance, the solution 606 may include a material that does not interact with or adversely affect the 3-D nano-particle assemblies 610. In any regard, as also shown in the diagram 600, a vibration 608 may be applied onto the apparatus 100. The vibration 608 may include a sonication applied through the solution 606 and/or a physical vibration of the application 100. Although not shown, the vibration 608 may be generated through any conventional vibration source suitable to generate sufficient vibrations to cause the 3-D nano-particle assemblies 610 to be detached from the nano-fingers 104. As shown in the diagram 602 (FIG. 6B), the vibration 608 is intended to cause the 3-D nano-particle assemblies 610 to be detached from the nano-fingers 104 and released into the solution 606 as denoted by the arrows 609.

According to an example, a layer of material may be provided on the tips 108 of the nano-fingers 104 to enhance release of the 3-D nano-particle assemblies 610 from the nano-fingers 104. The material may include, for instance, a fluorocarbon.

Figure 7A:
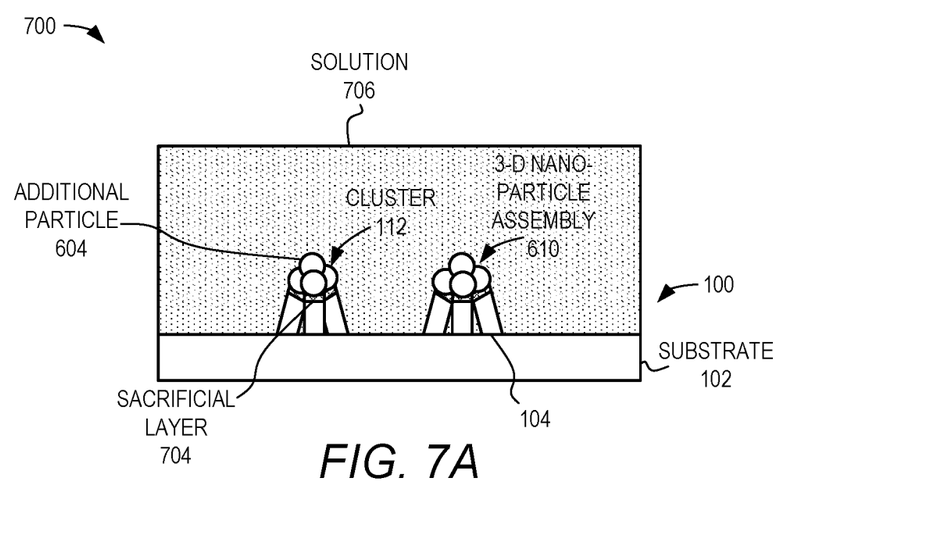
Figure 7B:
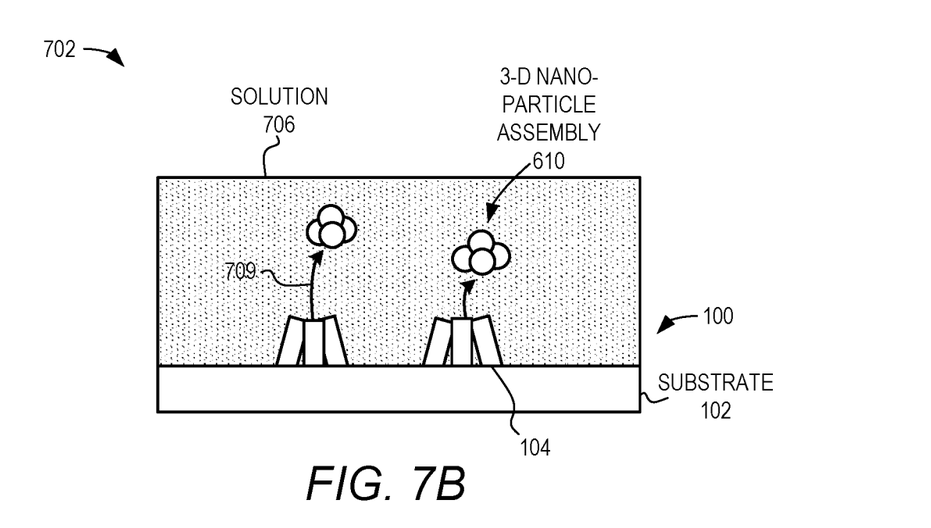

Turning now to FIGS. 7A and 7B, there are respectively shown diagrams 700 and 702 of various stages of a method for forming 3-D nano-particle assemblies 610, according to an example. The diagrams 700 and 702 are respectively similar to the diagrams 600 and 602 and thus, features having the same reference numerals will not be discussed with respect to FIGS. 7A and 7B. The diagrams 700 and 702 differ from the diagrams 600 and 602 in that, in the diagrams 700 and 702, a vibration 608 may not be applied onto the 3-D nano-particle assemblies 610. Instead, in the diagram 700, a sacrificial layer 704 is depicted as being provided between the tips 108 of the nano-fingers 104 and the clusters 112.

The sacrificial layer 704 may be deposited onto the tips 108 of the nano-particles 104 prior to deposition of the SES elements 106. Additionally, the sacrificial layer 704 may be deposited onto the tips 108 in any of the manners discussed above with respect to the deposition of the SES elements 106, or using alternative techniques such as spin coating or other standard microfabrication processes.

The apparatus 100 along with the 3-D nano-particle assemblies 610, are depicted as being positioned in a solution 706. The solution 706 may include any suitable type of material into which the 3-D nano-particle assemblies 610 may be released. In addition, the solution 706 may be a solution that is to dissolve the sacrificial layer 704 and may be selected based upon the materials with which the sacrificial layer 704 may be formed. By way of particular examples, the sacrificial layer 704 may include aluminum (Al) and the solution 706 may include dilute hydrochloric acid (HCl) solution, the sacrificial layer 704 may include titanium (Ti) and the solution 706 may include dilute hydrofluoric acid (HF), the sacrificial layer 704 may include polymethyl methacrylate (PMMA) and the solution 706 may include a solvent, etc. In any regard, as shown in the diagram 702 (FIG. 7B), the sacrificial layer 704 is to be dissolved thereby causing the 3-D nano-particle assemblies 610 to be detached from the nano-fingers 104 and released into the solution 706 as denoted by the arrows 709.

Figure 8A:
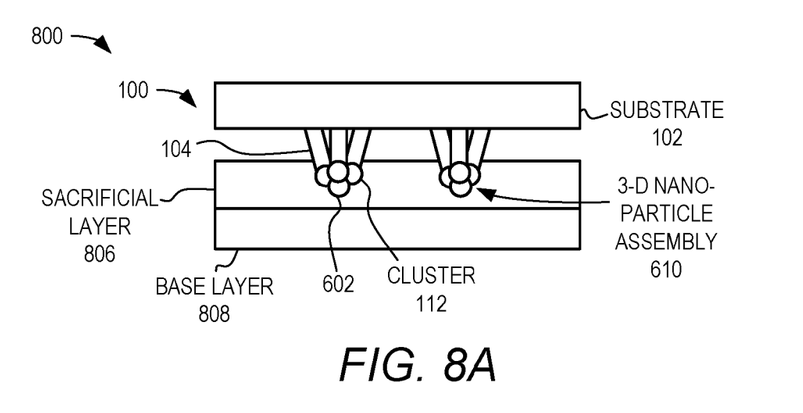
Figure 8B:
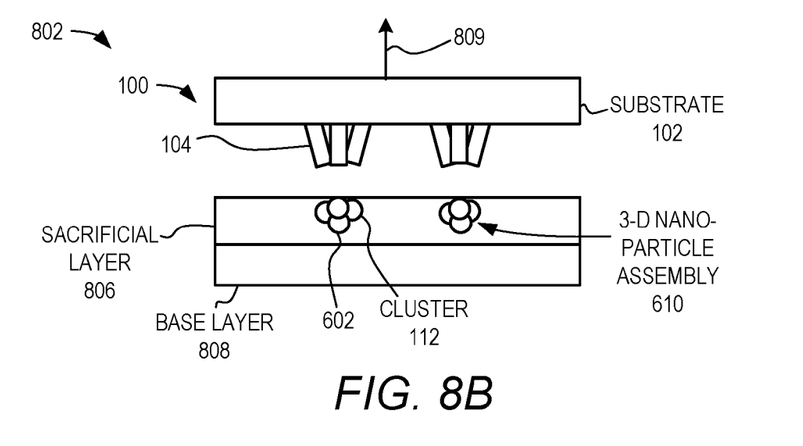
Figure 8C:
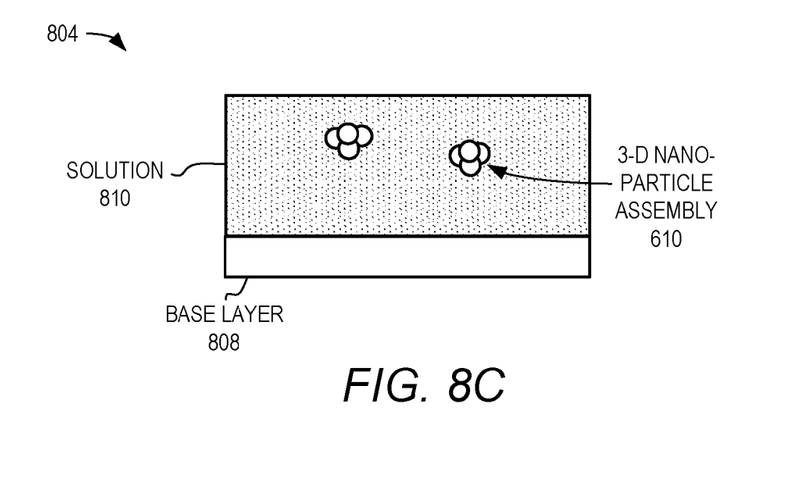

Turning now to FIGS. 8A-8C, there are respectively shown diagrams 800, 802, 804 of various stages of a method for forming 3-D nano-particle assemblies 610, according to an example. As shown in the diagram 800 (FIG. 8A), the 3-D nano-particle assemblies 610 are depicted as being imprinted into a sacrificial layer 806, which is provided on a base layer 808. The base layer 808 may be formed of any suitable materials such as any of the materials listed above with respect to the substrate 102. As such, and according to an example, the diagram 800 may depict a stage following the formation of the 3-D nano-particle assemblies 610 in FIGS. 4A and 5A.

According to an example, the sacrificial layer 806 may be a fluid material into which the 3-D nano-particle assemblies 610 may be inserted. The sacrificial layer 806 may be cured to trap the 3-D nano-particle assemblies 610 inside the sacrificial layer 806. By way of particular example, the sacrificial layer 806 may include polymethyl methacrylate (PMMA).

As shown in the diagram 802 (FIG. 8B), the 3-D nano-particle assemblies 610 may be separated from the nano-fingers 104 through relative movement of the substrate 102 and the nano-fingers 104 with respect to the sacrificial layer 806. According to an example, the substrate 102 and the nano-fingers 104 may be moved as noted by the arrow 809 away from the sacrificial layer 806, while the sacrificial layer 806 is held in place. Alternatively, the sacrificial layer 806 and the base layer 808 may be moved away from the substrate 102 while the substrate 102 is held in place. In any regard, the bond between the nano-fingers 104 and the substrate 102 may substantially be stronger than the bond, if any, between the nano-fingers 104 and the 3-D nano-particle assemblies 610. As such, when one of the substrate 102 and the sacrificial layer 806 is moved away from the other, the 3-D nano-particle assembly 610 may separate or detach from the nano-fingers 104 as shown in FIG. 8B.

Following separation of the 3-D nano-particle assemblies 610 from the nano-fingers 104, a solution 810 that is to dissolve the sacrificial layer 806 may be introduced onto the sacrificial layer 806. By way of example, the solution 810 may include a solvent, such as acetone, toluene, etc. The solution 810 is depicted in the diagram 804 (FIG. 8C), which depicts a stage of the method following the dissolving of the sacrificial layer 806. The diagram 804 also shows that the 3-D nano-particle assemblies 610 have been released from the sacrificial layer 806.

Figure 9A:
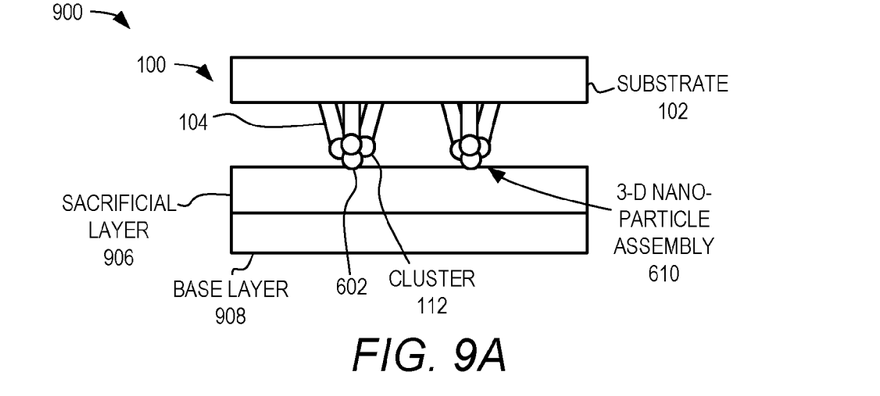
Figure 9B:
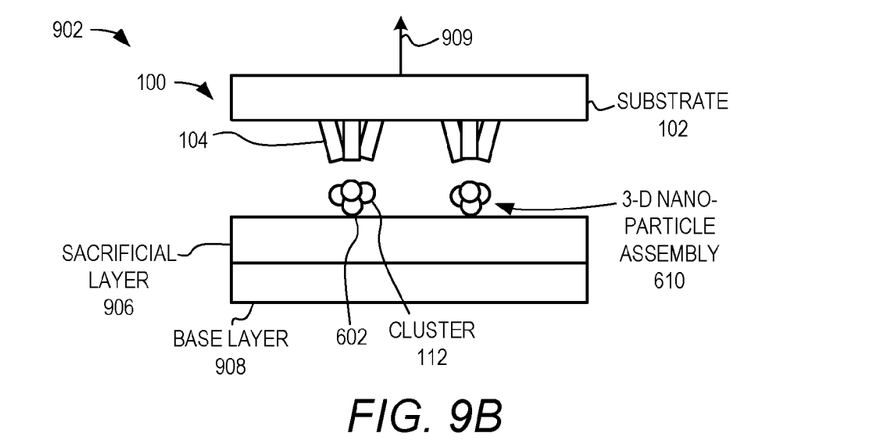
Figure 9C:
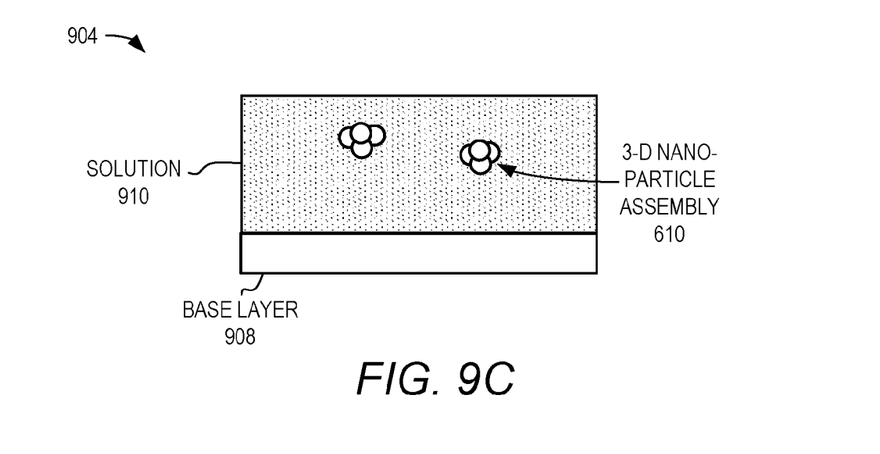

Turning now to FIGS. 9A-9C, there are respectively shown diagrams 900, 902, 904 of various stages of a method for forming 3-D nano-particle assemblies 610, according to an example. As shown in the diagram 900 (FIG. 9A), the 3-D nano-particle assemblies 610 are depicted as being imprinted onto a sacrificial layer 906, which is provided on a base layer 908. As such, and according to an example, the diagram 900 may depict a stage following the formation of the 3-D nano-particle assemblies 610 in FIGS. 4A and 5A.

According to an example, the sacrificial layer 906 may include a metal material, such as aluminum, titanium, etc. The sacrificial layer may also include a thin oxide layer on top to assist in the binding chemistry. In addition, the 3-D nano-particle assemblies 610 may be bonded to the sacrificial layer 906 through use of a binding molecule, such as, 3-mercaptopropyltrimethoxysilane (MPTMS).

As shown in the diagram 902 (FIG. 9B), the 3-D nano-particle assemblies 610 may be separated from the nano-fingers 104 through relative movement of the substrate 102 and the nano-fingers 104 with respect to the sacrificial layer 906. According to an example, the substrate 102 and the nano-fingers 104 may be moved as noted by the arrow 909 away from the sacrificial layer 906, while the sacrificial layer 906 is held in place. Alternatively, the sacrificial layer 906 and the base layer 908 may be moved away from the substrate 102 while the substrate 102 is held in place. In any regard, the bond between the nano-fingers 104 and the substrate 102 may substantially be stronger than the bond, if any, between the nano-fingers 104 and the 3-D nano-particle assemblies 610. In addition, the bond between the 3-D nano-particle assemblies 610 and the sacrificial layer 906 may substantially be stronger than the bond, if any, between the 3-D nano-particle assemblies 610 and the nano-fingers 104. As such, when one of the substrate 102 and the sacrificial layer 906 is moved away from the other, the 3-D nano-particle assembly 610 may separate or detach from the nano-fingers 104 as shown in FIG. 9B.

Following separation of the 3-D nano-particle assemblies 610 from the nano-fingers 104, a solution 910 that is to dissolve the sacrificial layer 906 may be introduced onto the sacrificial layer 906. By way of example, the solution 910 may include an acid, such as HCl (hydrochloric acid), HF (hydrofluoric acid), etc. The solution 910 is depicted in the diagram 904 (FIG. 9C), which may depict a stage of the method following the dissolving of the sacrificial layer 906. The diagram 904 also shows that the 3-D nano-particle assemblies 610 have been released from the sacrificial layer 906.

Although particular reference has been made in FIGS. 6A-9C to the detachment of 3-D nano-particle assemblies 610 including the structures depicted in FIGS. 4A-5C, it should be understood that some of the concepts discussed with respect to FIGS. 6A-9C may equivalently be applied to detach the clusters 112 and the protective coatings 308 depicted in FIGS. 3A-3C.

Following separation of the 3-D nano-particle assemblies 610 from the nano-fingers 104 in any of the manners discussed above, and in the case of FIGS. 3A-3C, following the linking of multiple clusters 112, the 3-D nano-particle assemblies 320, 610 may be employed in a sensing and/or tagging system. Particularly, for instance, the 3-D nano-particle assemblies 320, 610 may have trapped therein a reporter molecule, which may have been introduced between the SES elements 106 prior to partially collapsing of the nano-fingers 104 as discussed above. In addition, surfaces of the 3-D nano-particle assemblies 320, 610, for instance, the SES elements 106 and/or the protective coatings 308, may be functionalized to preferentially bond to specific regions, e.g., target tissues/cells in a human body. Thus, for instance, the 3-D nano-particle assemblies 320, 610 disclosed herein may be employed to map the specific regions.

Although described specifically throughout the entirety of the instant disclosure, representative examples of the present disclosure may have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A method for forming three-dimensional (3-D) nano-particle assemblies, said method comprising:
   depositing a plurality of surface-enhanced spectroscopy (SES) elements onto respective tips of a plurality of nano-fingers, wherein the nano-fingers are arranged in sufficiently close proximities to each other to enable the tips of groups of adjacent ones of the nano-fingers to come into sufficiently close proximities to each other to enable the SES elements on the tips to be bonded together when the nano-fingers are partially collapsed;
   causing the nano-fingers to partially collapse toward adjacent ones of the nano-fingers to cause a plurality of SES elements on respective groups of the nano-fingers to be in relatively close proximities to each other and form respective clusters of SES elements;
   introducing additional particles that are to attach onto the clusters of SES elements; and
   causing the clusters of SES elements to detach from the nano-fingers.

2. The method according to claim 1, wherein causing the nano-fingers to partially collapse onto adjacent ones of the nano-fingers further comprises causing respective groups of at least three nano-fingers to partially collapse toward each other to cause at least some of the respective clusters of SES elements to include at least three SES elements.

3. The method according claim 1, wherein the additional particles comprise protective coatings, and wherein introducing the additional particles further comprises applying the protective coatings on first sides of the clusters of SES elements prior to detaching the clusters of SES elements from the nano-fingers.

4. The method according to claim 3, further comprising:
   functionalizing the protective coatings to attach to target molecules.

5. The method according to claim 3, wherein the protective coatings are not provided on a second side of each of the clusters that is opposite the first side of each of the clusters and wherein the second side of one of the clusters is bonded to the second side another one of the clusters to form one of the 3-D nano particle assemblies.

6. The method according to claim 5, wherein causing the nano-fingers to partially collapse onto adjacent ones of the nano-fingers further comprises causing respective groups of at least three nano-fingers to partially collapse toward each other to cause at least some of the respective clusters of SES elements to include at least three SES elements.

7. The method according to claim 3, further comprising:
   releasing the clusters of SES elements into a solution that contains a plurality of linker molecules that are to bind to exposed portions of the clusters of SES elements to cause multiple clusters of SES elements to bind together via the linker molecules.

8. The method according to claim 1, wherein an electrically conductive layer is provided on a surface of the substrate and wherein the additional particles comprise electrically charged functional molecules, said method further comprising:
   applying a voltage through the electrically conductive layer to cause the clusters of SES elements to have an electrical charge that is oppositely biased from the electrically charged functional molecules and cause the electrically charged functional molecules to be attracted to and bind to the clusters of SES elements.

9. The method according to claim 1, wherein the additional particles comprise magnetic particles and wherein the plurality of SES elements comprise magnetic particles, and wherein introducing the additional particles onto the clusters of SES elements further comprises introducing the additional particles onto the clusters of SES elements such that the additional particles attach onto the clusters of SES elements through operation of magnetic forces between the additional particles and the clusters of SES elements.

10. The method according to claim 1, wherein the additional particles comprise binding molecules, said method further comprising:
    introducing a solution containing the binding molecules onto the SES elements and the nano-fingers prior to partially collapsing the nano-fingers; and
    wherein causing the nano-fingers to partially collapse comprises causing the nano-fingers to partially collapse to cause the binding molecules to be trapped between the SES elements of at least some of the clusters of SES elements.

11. The method according to claim 1, wherein causing the clusters of SES elements to detach from the nano-fingers further comprises causing the clusters of SES elements and the nano-fingers to vibrate, wherein the vibration is to cause the clusters of SES elements to detach from the nano-fingers.

12. The method according to claim 1, said method further comprising:
    applying sacrificial layers on the tips of the nano-finger, and wherein depositing the SES elements further comprises depositing the SES elements onto the sacrificial layers; and
    wherein causing the clusters of SES elements to detach from the nano-fingers further comprises dissolving the sacrificial layers to detach the clusters of SES elements from the plurality of nano-fingers.

13. The method according to claim 1, wherein causing the clusters of SES elements to detach from the nano-fingers further comprises:
    transferring the clusters of SES elements at least one of onto and into a sacrificial layer such that the clusters of SES elements are at least one of bound to and trapped within the sacrificial layer; and
    dissolving the sacrificial layer to release the clusters of SES elements.

14. The method according to claim 1, further comprising:
    forming the 3-D nano-particle assemblies through attachment of the additional particles onto the clusters of SES elements, wherein the 3-D nano-particle assemblies have substantially uniform configurations with respect to each other.

15. A method for forming a three-dimensional (3-D) nano-particle assembly, said method comprising:
    obtaining a substrate on which at least two nano-fingers extend from a surface of the substrate;
    depositing a surface-enhanced spectroscopy (SES) element onto each of the tips of the nano-fingers;
    causing the nano-fingers to partially collapse toward each other to cause the SES elements on the tips of the nano-fingers to come into sufficiently close proximity to each other to enable the SES elements to bond to each other and form a cluster of SES elements;
    introducing additional particles onto the SES elements; and
    causing the cluster of SES elements to detach from the nano-fingers, wherein the additional particles are introduced onto the SES elements at least one of prior to and following the causing of the nano-fingers to partially collapse toward each other or at least one of prior to and following the detaching of the cluster of SES elements from the nano-fingers.

16. The method according to claim 15, wherein causing the nano-fingers to partially collapse onto adjacent ones of the nano-fingers further comprises causing respective groups of at least three nano-fingers to partially collapse toward each other to cause the cluster of SES elements to include at least three SES elements.

17. The method according claim 15, wherein the additional particles comprise protective coatings, and wherein introducing the additional particles further comprises applying the protective coatings on a first side of the cluster of SES elements prior to detaching the clusters of SES elements from the nano-fingers.

18. The method according to claim 17, further comprising functionalizing the protective coatings to attach to target molecules.

19. The method according to claim 17, wherein the protective coatings are not provided on a second side of the cluster that is opposite the first side of the cluster and wherein the second side of the cluster is bonded to the second side of another cluster to form one of the 3-D nano particle assemblies.

20. The method according to claim 19, wherein causing the nano-fingers to partially collapse onto adjacent ones of the nano-fingers further comprises causing respective groups of at least three nano-fingers to partially collapse toward each other to cause the cluster of SES elements to include at least three SES elements.

* * * * *

UNITED STATES PATENT AND TRADEMARK OFFICE
CERTIFICATE OF CORRECTION

PATENT NO. : 9,739,717 B2  
APPLICATION NO. : 15/289050  
DATED : August 22, 2017  
INVENTOR(S) : Steven J. Barcelo et al.

It is certified that error appears in the above-identified patent and that said Letters Patent is hereby corrected as shown below:

In the Claims

In Column 13, Line 30, in Claim 3, delete "according claim" and insert -- according to claim --, therefor.

In Column 14, Line 10, in Claim 17, delete "according claim" and insert -- according to claim --, therefor.

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*